United States Patent [19]

Murphy

[11] Patent Number: 4,804,764
[45] Date of Patent: Feb. 14, 1989

[54] PROCESS FOR PRODUCING 2,3,5,6-TETRACHLOROPYRIDINE

[75] Inventor: Frank H. Murphy, Alvin, Tex.

[73] Assignee: The Dow Chemical Company, Midland, Mich.

[21] Appl. No.: 49,487

[22] Filed: May 14, 1987

Related U.S. Application Data

[62] Division of Ser. No. 909,443, Sep. 19, 1986, Pat. No. 4,703,123.

[51] Int. Cl.$^4$ ............... C07D 213/12; C07D 213/14
[52] U.S. Cl. .................................. 546/345; 546/329
[58] Field of Search ................................ 546/345

[56] References Cited

U.S. PATENT DOCUMENTS 4,703,123 10/1987 Murphy ........................ 546/345

*Primary Examiner*—Alan L. Rotman
*Attorney, Agent, or Firm*—Joseph T. Majka; D. Wendell Osborne

[57] ABSTRACT

In accordance with the present invention, 2,3,5,6-tetrachloropyridine is advantageously prepared by contacting pentachloropyridine in a solvent selected from the group consisting of alkylnitriles, water, alkylsulfoxides, tetramethylsulfone, C-1 to C-5 alcohols, alkyl carbonates and mixtures thereof, in the presence of an ammonium salt of an organic or inorganic acid with about 0.7 to about 1.1 g atoms of zinc per mole of pentachloropyridine.

7 Claims, No Drawings

PROCESS FOR PRODUCING 2,3,5,6-TETRACHLOROPYRIDINE

This is a divisional of application Ser. No. 909,443 filed Sept. 19, 1986 now U.S. Pat. No. 4,703,123.

BACKGROUND OF THE INVENTION

The present invention relates to an improved process for preparing 2,3,5,6-tetrachloropyridine from pentachloropyridine(PCP).

2,3,5,6-Tetrachloropyridine is a valuable commercial product which can be used for the production of insecticidal formulations. Furthermore, 2,3,5,6-tetrachloropyridine is used as an intermediate for producing herbicidally effective α-[4-(3',5',6'-trichloropyrid-2'-yloxy)-phenoxy]-alkanecarboxylic acids and derivatives thereof. The production and use of such α-[4-(3',5',6'-trichloropyrid-2'-yloxy)-phenoxy]-alkanecarboxylic acids and derivatives thereof are described, for example, in the U.S. Pat. No. 4,133,675.

Methods are known for preparing 2,3,5,6-tetrachloropyridine from pentachloropyridine. U.S. Pat. No. 3,993,654 teaches a process of preparing tetrachloropyridine by reacting pentachloropyridine, zinc and hydrochloric acid in an aqueous medium at a temperature of at least 110° C. under at least autogeneous pressure. U.S. Pat. No. 4,259,495 teaches a process of preparing 2,3,5,6-tetrachloropyridine by reacting pentachloropyridine with zinc in an alkanephosphoric acid dialkyl ester solvent in the presence of an ammonium salt. Although achieving good yields, this process has the serious disadvantage that it is difficult to separate the alkanephosphoric acid dialkyl ester solvent from the desired 2,3,5,6-tetrachloropyridine product without elaborate or sophisticated separation apparatus. Another disadvantage is that the high boiling point of the alkanephosphoric acid dialkyl ester solvent makes this solvent difficult to recycle in industrial processes, requiring incineration or land disposal of an otherwise expensive and polluting solvent. U.S. Pat. No. 4,259,495 also discloses that the process employs 1.2 to 1.6 gram-atoms of zinc per mole of pentachloropyridine. Zinc is one of the most expensive reactants used in the process of making 2,3,5,6-tetrachloropyridine from pentachloropyridine. It would clearly be desirable to carry out a process which utilizes a solvent which can be readily recycled and which utilizes zinc even more efficiently than the process disclosed in U.S. Pat. No. 4,259,495 in order to reduce operating expenses involved with waste disposal and the cost of zinc.

SUMMARY OF THE INVENTION

In accordance with the present invention, 2,3,5,6-tetrachloropyridine is advantageously prepared by contacting pentachloropyridine in a solvent selected from the group consisting f alkylnitriles, water, alkylsulfoxides, tetramethylsulfone, C-1 to C-5 alcohols, alkyl carbonates and mixtures thereof, in the presence of an ammonium salt of an organic or inorganic acid with about 0.7 to about 1.1 g atoms of zinc per mole of pentachloropyridine.

Preferably, the solvent employed is an alkylnitrile, alkylsulfoxide, or a mixture thereof with water. Most preferably, the alkylnitrile solvent is acetonitrile and the alkylsulfoxide solvent is dimethylsulfoxide (DMSO). Preferably, the ammonium salt is ammonium chloride.

Also preferred is that the process employs about 1.0 g atom of zinc per mole of pentachloropyridine.

The process of the present invention has the advantage of utilizing solvents which are readily separated from the desired product and which lend themselves to conventional recycling procedures. The present process also has the unobvious advantage of utilizing zinc more efficiently than disclosed in previously known methods.

DETAILED DESCRIPTION OF THE EMBODIMENTS

The desired product 2,3,5,6-tetrachloropyridine is represented by the formula:

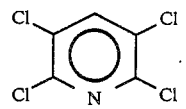

One of the requisite starting materials, pentachloropyridine, is represented by the formula:

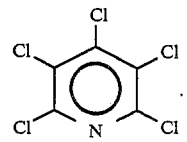

Readily recyclable solvents suitable for contacting pentachloropyridine with the requisite ammonium salt and zinc reactants should be those solvents which can readily be separated from the reaction mixture after completion of the reaction. Representative solvents suitable for such contacting include but are not limited to alkylnitriles, water, alkylsulfoxides, tetramethylsulfone, C-1 to C-5 alcohols, alkyl carbonates and mixtures thereof.

Suitable alkylnitriles which can be used according to the invention as solvents are of the formula R-C≡N, wherein R is C-1 to C-5 alkyl; the compound is acetonitrile wherein R is methyl.

Suitable alkylsulfoxides which can be used according to the invention as solvents are of the formula:

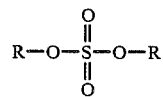

wherein R independently represents C-1 to C-5 alkyl, more preferably C-1 to C-3 alkyl. Most preferably, R is methyl, otherwise known as dimethylsulfoxide (DMSO).

Water, at least equivalent in quality to, that used for industrial purposes, is a solvent which can be used according to the invention.

Tetramethylene sulfone, as a solvent which can be used according to the invention, is represented by the formula:

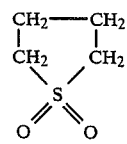

C-1 to C-5 alcohols which can be used according to the invention as solvents include, but are not limited to, methanol, ethanol, n-proponal, t-propanol, n-butanol, iso-butanol and n-pentanol, preferably iso-butanol.

Alkylcarbonates which can be used according to the invention as solvents are of the generic formula:

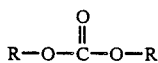

wherein R independently represents C1-C5 alkyl. Representative alkylcarbonates include, but are not limited to, dimethylcarbonate, methyl ethyl carbonate, diethyl carbonate, ethyl propyl carbonate and the like.

The process of the present invention can be conducted using the above-mentioned solvents in about technical grade or better quality. In certain instances, mixtures of the above solvents can be advantageously employed. Preferred mixtures include acetonitrile and water; and dimethylsulfoxide and water.

The amount of solvent to be employed in the process of the present invention is expressed as a ratio of pentachloropyridine to solvent. Generally, the process is conducted using, on a weight percentage basis, a ratio of 1:2 to about 1:200 or more (pentachloropyridine:solvent), preferably in a range of about 1:4 to about 1:20. Most preferably, the process is conducted employing a saturated solution of pentachloropyridine in the solvent, using sufficient solvent to just dissolve all the pentachloropyridine.

Within the temperature range of about 50° to about 175° C., in which the process according to the invention can be performed, temperatures of about 78° to about 120° C. are preferred.

The quarternary ammonium salts which can be used in the present invention contain, as the cation, the ammonium ion, or the sterically feasible derivatives derived therefrom by partial or complete replacement of the hydrogen atoms by alkyl and/or phenyl groups, wherein the phenyl groups can be unsubstituted or substituted by 1 to 3 simple substituents such as alkyl, alkoxy or halogen. The ammonium salts usable according to the invention contain as anion the radical of any inorganic or organic acid capable of forming ammonium salts, such as a strong inorganic or organic acid with a pka of 2 or less.

Advantageously applicable ammonium salts correspond to the formula:

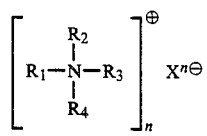

in which $R_1$, $R_2$, $R_3$ and $R_4$ are sterically feasible and can be identical or different and are each hydrogen, alkyl having 1 to 4 carbon atoms, or phenyl or substituted phenyl which is substituted by up to 3 halogens, or by alkyl groups having 1 to 4 carbon atoms or by alkoxy groups having 1 to 4 carbon atoms; X is an anion selected from the group: chloride, bromide, sulfate, hydrogen sulfate, phosphate, hydrogen phosphate, dihydrogen phosphate, acetate, propionate, butyrate, isobutyrate, oxalate, benzoate, benzenesulfonate and alkylsulfonates having 1 to 4 carbon atoms in the alkyl group; and n is 1 to 3 and corresponds to the number of negative charges of the respective anion X.

The amount of ammonium salt to be employed in the current process is in the weight ratio of about 1:1 to about 1:6, (pentachloropyridine:ammonium salt) preferably from about 1:2 to about 1:4.

Pressures within which the process of the present invention can be conducted range suitably from atmospheric up to the autogenous vapor pressure of the solvent at its boiling point.

The zinc to be used according to the invention is finely divided in the form of zinc chips or granules or preferably in the form of zinc dust.

The amount of zinc can range from about 0.7 to about 1.1 gram atoms of zinc per mole pentachloropyridine, preferably about 1.0 gram atoms of zinc per mole of pentachloropyridine in order to obtain optimum zinc utilization, while reacting most of the PCP.

The desired 2,3,5,6-tetrachloropyridine can be recovered from the reaction mixture by various procedures, depending in part on the type of solvent employed. Representative procedures include, but are not limited to one or more of distillation, extraction, phase separation, crystallization and filtration, preferably distillation and filtration where acetonitrile is employed as the solvent.

The following examples are presented to illustrate typical processes of the present invention, but the scope of the invention is not to be considered limited to the specific examples given.

EXAMPLE 1—ACETONITRILE SOLVENT AND AMMONIUM CHLORIDE

To a flask are added 35 grams (g) (0.139 mole (mol)) of pentachloropyridine (PCP) and 199 g of acetonitrile. The mixture is stirred vigorously and heated to reflux 978 degrees Centigrade (° C.)) to dissolve the PCP. To the reactive mixture is added 9.61 g (0.139 mol) of 93.7 percent pure metallic zinc dust, (g atom zinc:mole pentachloropyridine ratio is 1:1). A solution of 15.08 g (0.282 mol) ammonium chloride (NH4Cl) in 40.2 g water is added drop-wise over a 45 minute (min) period. After agitation for another 2.25 hours (hr), 17.74 g of 12 normal (N) hydrochloric acid is added, a distillation head is attached to the reaction flask, and 164 g of material is distilled out at an overhead temperature of 77-78° C. To the pot is added 137.5 g of 6.25N hydrochloric acid and the mixture is stirred for 1 hr. The chloropyridines precipitate out of solution as a white solid and are removed by vacuum filtration prior to drying to a constant weight in a vacuum oven. Analysis of the chloropyridines by gas chromatography gives a molar selectivity of the pentachloropyridine converted of:

99.35 percent (%) desired product, viz., 2,3,5,6-tetrachloropyridine (28.977 g)

0.22% to 2,3,5-trichloropyridine (0.054 g), 0.01% to 2,3,4,5-tetrachloropyridine (0.003 g), and 0.42% to 2,3,4,6-tetrachloropyridine (0.122 g), at 96.75 percent pentachloropyridine conversion. Of the metallic zinc used in the reaction. 95.61 percent reacts with chloropyridine with 91.71 percent resulting in the formation of 2,3,5,6-tetrachloropyridine. Of the metallic zinc added, 100 percent oxidizes during the reaction with 99.16 percent of it accounted for in the final products.

EXAMPLE 2—ACETONITRILE SOLVENT AND AMMONIUM ACETATE

To a flask are added 35 g (0.139 mol) of pentachloropyridine, 21.5 g (0.28 mol) ammonium acetate, 40 g water, and 200 g acetonitrile and the compounds are heated to reflux (78° C.) while being agitated vigorously. Subsequently, 9.75 g (0.140 mol) of 93.7 percent zinc dust, (g atom zinc: moles pentachloropyridine is 1:1), is added and the solution is refluxed for 3.58 hrs. After the reaction is complete, a distillation head is attached and 188 g of material is removed overhead. Water and perchloroethylene are added to the flask, partitioning the organic (341.2 g) and aqueous (336.2 g) phases. Analysis for chloropyridines in the organic phase by gas chromatography and for zinc in the aqueous phase by wet methods indicates a molar selectivity of the pentachloropyridine converted of:

96.90% to 2,3,5,6-tetrachloropyridine (27.899 g)
 0.19% to 3,5-dichloropyridine (0.037 g),
 0.46% to 2,3,5-trichloropyridine (0.111 g),
 0.15% to 2,3,6-trichloropyridine (0.36 g),
 0.07% to 2,3,4,5-tetrachloropyridine (0.020 g),
 2.23% to 2,3,4,6-tetrachloropyridine (0.642 g), and
at 95.07 percent pentachloropyridine conversion with 98.13 percent of the pentachloropyridine added accounted for in the final products. Of the metallic zinc used in the reaction, 95.61 percent reacts with chloropyridines with 91.72 percent resulting in the formation of 2,3,5,6tetrachloropyridine. Of the metallic zinc added, 100 percent oxidizes during the reaction.

EXAMPLE 3—WATER SOLVENT AND AMMONIUM CHLORIDE

A flask containing 115 g (0.458 mol) of pentachloropyridine, 31.61 g (0.453 mol) of 93.7 percent metallic zinc dust, (g atom zinc:moles pentachloropyridine is 1:1), 49 g (0.906 mol) ammonium chloride, and 125 g water is heated to reflux (100° C.) for 6.0 hrs while being agitated vigorously. The reaction mixture is quenched by adding 250 g of toluene and 280 g of water. Any solids remaining in the reaction mixture are filtered out (0.03 g) of the solution prior to the addition of 15 g of 12N hydrochloric acid, partitioning the aqueous and organic phases. Analysis for chloropyridines in the organic phase by gas chromatography and analysis for zinc in the aqueous phase by wet methods indicates a molar selectivity of the pentachloropyridine converted of:

96.88% to 2,3,5,6-tetrachloropyridine (90.073 g)
 0.12% to 3,5-dichloropyridine (0.076 g),
 0.96% to 2,3,5-trichloropyridine (0.751 g),
 0.23% to 2,3,6-trichloropyridine (0.180g),
 0.06% to 2,3,4,5-tetrachloropyridine (0.056 g),
 1.75% to 2,3,4,6-tetrachloropyridine (1.627 g), and
at a 93.60 percent pentachloropyridine conversion with 97.12 percent of the pentachloropyridine added accounted for in the final product. Of the metallic zinc used in the reaction, 95.76 percent reacts with chloropyridine with 91.47 percent resulting in the formation of 2,3,5,6-tetrachloropyridine. Of the metallic zinc added, 100 percent oxidizes during the reaction with 99.16 percent of it accounted for in the final reaction products.

EXAMPLE 4—DIMETHYLSULFOXIDE SOLVENT AND AMMONIUM CHLORIDE

A flask containing 35.01 g (0.139 mol) of pentachloropyridine dissolved in 220 g dimethylsulfoxide is heated to 100° C. To the flask is added 9.62 g (0.139 mol) of 93.7 percent metallic zinc dust, (g atoms zinc: moles pentachloropyridine is 1:1). A solution of 9.73 g (0.182 mol) ammonium chloride in 29.6 g of water is added drop-wise with vigorous agitation over a 40 min period. The reaction mixture is maintained at 100° C. for an additional 1.75 hr, filtered to remove any solids (0.2 g) and the chloropyridines are precipitated in the reaction mixture by adding 360 g water and 300 g of 6N hydrochloric acid. The chloropyridines are filtered out of solution and dried in a vacuum oven to constant weight (30.0 g). Analysis of the chloropyridines by gas chromatography indicates a molar selectivity of the pentachloropyridine converted of:

94.6% to 2,3,5,6-tetrachloropyridine (27.585 g)
 0.29% to 2,3,5-trichloropyridine (0.071 g),
 3.29% 2,3,4,5-tetrachloropyridine (0.956 g), and
 1.46% 2,3,4,6-tetrachloropyridine (0.424 g),
at 96.18 percent pentachloropyridine conversion with 99.6 percent of the pentachloropyridine added accounted for in the final product. Of the metallic zinc used in the reaction 97.37 percent reacts with chloropyridine with 92.20 percent resulting in the formation of 2,3,5,6-tetrachloropyridine. Of the metallic zinc added, 100 percent, oxidizes and 98.90 percent is accounted for in the final product.

EXAMPLE 5—ISOBUTANOL SOLVENT AND AMMONIUM CHLORIDE

A flask containing 40.0 g (0.159 mol) of pentachloropyridine, 11.03 g 90.159 mol) of 93.7 percent metallic zinc dust (g atom zinc:moles pentachloropyridine is 1:1) and 135 g isobutanol is heated to reflux (92° C.) and the reactants are vigorously agitated. A solution of 17.03 g (0.32 mol) ammonium chloride in 48.67 g water is added drop-wise to the reaction mixture over 30 min. period. The reaction mixture is refluxed for 4.42 hrs, then quenched with 170 g toluene and 227 g water. Any solids present are filtered out, and the organic phase is separated from the aqueous phase. Analysis of the organic phase by gas chromatography indicates a molar selectivity of the pentachloropyridine converted of:

91.02% to 2,3,5,6-tetrachloropyridine (31.418 g)
 0.19% to 3-chloropyridine (0.34 g),
 0.54% to 3,5-dichloropyridine (0.127 g),
 5.13% to 2,3,5-trichloropyridine (1.490 g),
 0.26% to 2,3,6-trichloropyridine (0.075 g),
 0.33% to 2,3,4,5-tetrachloropyridine (0.114 g), and
 2.54% to 2,3,4,6-tetrachloropyridine (0.877 g),
at 92.21 percent pentachloropyridine conversion with 98.94 percent of the pentachloropyridine added accounted for in the final product. Of the metallic zinc used in the reaction, 99.45 percent reacts with chloropyridine with 84.57 percent resulting in the formation of 2,3,5,6-tetrachloropyridine. Of the metallic zinc added, 99.83 percent oxidizes and 96.03 percent is accounted for in final reaction products.

EXAMPLE 6—TETRAMETHYLENE SULFONE AND AMMONIUM CHLORIDE

A flask containing 35.01 g (0.139 mol) of pentachloropyridine, 9.62 g (0.139 mol) of 93.7 percent metallic zinc dust, (g atoms zinc:moles pentachloropyridine is 1:1), and 249.1 g of tetramethylene sulfone (sulfolane) is heated to 90° C. and the reactants are vigorously agitated. A solution of 9.68 g (0.181 mol) ammonium chloride in 29.2 g water is added over a period of 35 min and the temperature of the reaction mixture is maintained at 90° C. for an additional 65 min. Any insoluble material is removed from the heated reaction mixture by filtration (0.74 g) (at 76.9 percent Zn and 53.9 percent metallic Zn). The reaction mixture is quenched with 694 g water and 7 g 12N hydrochloric acid, agitated for 1 hour (hr), the precipitated chloropyridines are removed by vacuum filtration and dried in a vacuum oven. Analysis of the chloropyridines by gas chromatography indicates a molar selectivity of the pentachloropyridine converted of:

89.23% to 2,3,5,6-tetrachloropyridine (23.911 g)
5.18% to 2,3,5-trichloropyridine (1.168 g),
0.99% to 2,3,6-trichloropyridine (0.223 g),
0.32% to 2,3,4,5-tetrachloropyridine (0.086 g), and
4.27% to 2,3,4,6-tetrachloropyridine (1.144 g), at 88.70 percent pentachloropyridine conversion with 96.10 percent of the pentachloropyridine added accounted for in the final product. Of the metallic zinc oxidized 99.47 percent reacted with chloropyridine with 83.59 percent resulting in the formation of 2,3,5,6-tetrachloropyridine. Of the metallic zinc added, 85.59 percent oxidizes with 96.03 percent being accounted for in the final products.

EXAMPLE 7—ACETONITRILE SOLVENT AND AMMONIUM CHLORIDE

AT REDUCED ZINC:PENTACHLOROPYRIDINE

A flask containing 35.2 g (0.140 mol) of pentachloropyridine, 15.0 g (0.28 mol) ammonium chloride, 56.5 g water, and 201.3 g acetonitrile is heated to reflux (78° C.) and the reactants are agitated vigorously. To the reaction mixture is added 7.26 g (0.104 mol) of 93.7 percent metallic zinc dust, (g atom zinc:moles pentachloropyridine is 0.74:1) and the reaction mixture is refluxed for 4.40 hrs. The heated reaction mixture is filtered to remove solids (0.17 g of material is recovered, whose analysis indicated 75.0 percent zinc). A distillation head is attached to the reaction flask and 222.1 g of material is removed overhead. Water and toluene are added to the flask and the organic and aqueous phases are separated. Analysis of chloropyridines in the organic phase by gas chromatography and for zinc in the aqueous phase by wet methods indicated a molar selectivity of the pentachloropyridine converted of:

97.27% to 2,3,5,6-tetrachloropyridine (20.868 g)
0.05% to 3,5-dichloropyridine (0.007 g),
0.33% to 2,3,5-trichloropyridine (0.060 g),
0.04% to 2,3,6-trichloropyridine (0.007 g),
0.05% to 2,3,4,5-tetrachloropyridine (0.011 g), and
2.25% to 2,3,4,6-tetrachloropyridine (0.483 g), at 70.63 percent pentachloropyridine conversation with 98.23 percent of the pentachloropyridine added accounted for in the final product. Of the metallic zinc, used in the reaction, 97.41 percent reacts with chloropyridine with 94.30 percent resulting in the formation of 2,3,5,6-tetrachloropyridine. Of the metallic zinc added, 98.10 percent oxidizes with 99.37 percent being accounted for in the final products.

EXAMPLE 8—ACETONITRILE SOLVENT AND AMMONIUM CHLORIDE

AT REACTION TEMPERATURE OF 60° C.

To a reactor is added 35.0 g (0.139 mol) of pentachloropyridine, 9.62 g (0.139 mol) of 93.7 percent metallic zinc dust (g atom zinc:moles pentachloropyridine is 1:1), 14.9 g (0.278 mol) ammonium chloride, 41.7 g water and 202 g acetonitrile. The reactants are agitated, heated and maintained at a temperature of 60° C. for 7.0 hrs. Analysis for chloropyridines by gas chromatography and for zinc by wet methods indicated a molar selectivity of the pentachloropyridine converted of:

99.68% to tetrachloropyridines (30.106 g), and
0.32% to 2,3,5-trichloropyridine (0.081 g), at a pentachloropyridine conversion of 73.4 percent.

EXAMPLE 9—ACETONITRILE SOLVENT AND AMMONIUM CHLORIDE AT A REACTION TEMPERATURE OF 145° C.

To a two liter Parr reactor is added 190.09 g (0.760 mol) of pentachloropyridine, 80.97 g (1.52 mol) ammonium chloride, 260 g water, 52.89 g (0.760 mol) of 93.7 percent metallic zinc dust, (g atom zinc:moles pentachloropyridine is 1:1) and 814 g acetonitrile. The reactor is sealed, the reactants agitated, the temperature of the reaction mixture is raised to 145° C. within 24 min, and maintained at that temperature for 64 min. The reactor is allowed to cool to room temperature, the contents are transferred to a flask equipped with a distillation apparatus and 964 g of material are removed overhead. Then 500 g toluene is added to the flask and the organic and aqueous layers that form are separated. Analysis of the aqueous phase for zinc by wet methods, and analysis of the organic phase for chloropyridines by gas chromatography indicates a molar selectivity of the pentachloropyridine converted of:

88.67% to 2,3,5,6-tetrachloropyridine (130.541 g))),
1.34% to 3,5-dichloropyridine (1.346 g),
0.01% to 2,4,6-trichloropyridine (0.012 g),
3.20% to 2,3,5-trichloropyridine (3.963 g),
1.23% to 2,3,6-trichloropyridine (1.523 g),
0.11% to 2,3,4,5-tetrachloropyridine (0.162 g),
2.31% to 2,3,4,6-tetrachloropyridine (3.401 g),
0.05% to 2-aminotetrachloropyridine (0.079 g), and
3.08 percent 4-aminotetrachloropyridine (4.848 g) at 89.75 percent pentachloropyridine conversion with 95.90 percent of the pentachloropyridine added accounted for in the final product. Of the metallic zinc oxidized, 93.04 percent reacted with chloropyridine with 79.34 percent resulting in the formation of 2,3,5,6-tetrachloropyridine. Of the metallic zinc added, 100 percent is oxidized in the course of the reaction with 93.4 percent accounted for in the final products.

Upon repeating Examples 1-9 utilizing any of the suitable ammonium salts and solvent cited hereinbefore in place of those utilized in the Examples, substantially the same excellent results are obtained regarding formation of the desired 2,3,5,6-tetrachloropyridine.

What is claimed is:

1. A process for preparing 2,3,5,6--tetrachloropyridine, comprising contacting pentachloropyridine in water and in the presence of a quaternary ammonium salt with about 0.7 to about 1.1 gram atoms of zinc per mole pentachloropyridine.

2. The process of claim 14 wherein a solvent selected from the group consisting of C-1 to C-5 alkylnitrile, C-1 to C-5 alkylsulfoxide, tetramethylene sulfone, a C-1 to C-5 alcohol, a C-1 to C-5 alkylcarbonate or a mixture thereof is employed in combination with the water.

3. The process of claim 14, wherein the ammonium salt is of an inorganic acid.

4. The process of claim 14 wherein the ammonium salt is ammonium chloride

5. The process of claim 14 conducted using between about 0.9 to about 1.1 gram atoms of zinc per mole of pentachloropyridine.

6. The process of claim 14, conducted using about 1.0 g atoms of zinc per mole of pentachloropyridine.

7. The process of claim 14 wherein the ammonium salt is ammonium chloride and the process is conducted using between about 0.9 to about 1.1 g atoms of zinc per mole of pentachloropyridine.

* * * * *